United States Patent [19]
Longo

[11] Patent Number: 6,139,228
[45] Date of Patent: Oct. 31, 2000

[54] KEYLESS CHUCK ASSEMBLY FOR A ROTARY DRIVEN TOOL

[75] Inventor: Paul T. Longo, Kalamazoo, Mich.

[73] Assignee: Stryker Corporation, Kalamazoo, Mich.

[21] Appl. No.: 09/206,110

[22] Filed: Dec. 4, 1998

[51] Int. Cl.⁷ .............................. B23B 31/06; B23B 45/00
[52] U.S. Cl. ......................... 408/240; 279/150; 279/902; 408/710
[58] Field of Search ..................................... 279/150, 902; 408/710, 239 R, 239 A, 240; 409/139, 182; 74/527; 188/69

[56] References Cited

U.S. PATENT DOCUMENTS

| | | | |
|---|---|---|---|
| 2,211,216 | 8/1940 | Oster | 279/147 |
| 2,536,017 | 1/1951 | Bamberger | 188/69 |
| 3,798,775 | 3/1974 | Weinberg et al. | 433/85 |
| 3,872,951 | 3/1975 | Hastings, Jr. | 188/69 |
| 4,526,497 | 7/1985 | Hatfield | 279/150 |
| 4,620,539 | 11/1986 | Andrews et al. | 279/150 |
| 5,860,775 | 1/1999 | Kim | 408/124 |

*Primary Examiner*—Steven C. Bishop
*Attorney, Agent, or Firm*—Flynn, Thiel, Boutell & Tanis, P.C.

[57] ABSTRACT

A chuck assembly (22) for releasably attaching a cutting accessory (23) to a rotary driven tool such as a surgical drill (20). The chuck assembly includes a chuck head (30) from which a drive spindle (36) extends rearwardly. Clamping jaws (34) extend from the front end of the chuck head to hold the cutting accessory in place. The chuck head, the drive spindle and the clamping jaws can rotate in unison about a common axis of rotation. Alternatively, the chuck head and the drive spindle can be rotated relative to each other around this common axis to lock and unlock the jaws. A spindle lock housing (41) is located between the chuck head and the drill to which the chuck head is attached. The drive spindle (36) extends through the spindle lock housing (41). A moveable switch (88) is mounted to the spindle lock housing (41). The switch can be positioned to engage the drive spindle to prevent rotation of the spindle. This makes manual unlocking and locking of the jaws possible when it is necessary to switch cutting accessories.

20 Claims, 8 Drawing Sheets

KEYLESS CHUCK ASSEMBLY FOR A ROTARY DRIVEN TOOL

FIELD OF THE INVENTION

This invention relates generally to a keyless chuck assembly that is used to hold a cutting accessory to a rotary driven tool such as a surgical tool. More particularly, this invention is directed to a keyless chuck assembly that is simple to use and that has safety features to prevent its improper use.

BACKGROUND OF THE INVENTION

An integral sub-assembly of most rotary driven tools, such as surgical drills, are their chuck assemblies. The chuck assembly is the part of the tool that holds a cutting accessory. For example, the cutting accessories used with surgical drills are drill bits, burs and wires. A typical chuck assembly includes a housing which contains a drive spindle. A set of jaws, also located in the housing, are mounted to the drive spindle. A linkage assembly opens and closes the jaws so that they can be used to grasp the accessory the tool is employed to drive. Once the accessory is mounted to the chuck assembly, the rotational power developed by a shaft of the motor internal to the tool is transferred through the drive spindle to the accessory. Providing rotary driven tools with chucks makes it possible to use these tools with many different types of cutting accessories.

In recent years, it has become popular to provide rotary driven tools with keyless chuck assemblies. A keyless chuck assembly is designed so that, when the chuck housing is held stable and its drive spindle is rotated, the jaws move together or move apart. Keyless chuck assemblies replace older, keyed chucks that require a key to lock and unlock the chuck jaws. One particular application in which keyless chuck assemblies are particularly popular is their use with powered surgical drills. An advantage of providing a surgical tool with keyless chuck is that it eliminates the need to bring a key into the surgical suite. Still another advantage of providing a keyless chuck is that this type of chuck is typically easier and quicker to lock and unlock than the keyed chucks that preceded it.

While keyless chucks have proven useful in surgical suites and in other environments where powered tools are used, there are some limitations associated with many currently available chucks. For example, in order to lock or unlock a chuck when it is attached to a tool, it is necessary to simultaneously hold the chuck housing stable while actuating the tool in order to cause the rotation of the drive spindle. When the chuck jaws fully close, lock tight against the complementary cutting accessory, the motive force generated by the tool is abruptly transferred to the chuck housing. Since the individual is still holding the housing, this individual is subjected to a physical jolt. Sometimes this jolt can be so great that it causes the gloves of the person holding the tool to tear. Once this tearing occurs, the individual must leave the surgical field.

Recently, at least in the surgical environment, it has become desirable to provide chuck assemblies to which a cutting accessory has already been preloaded. These chuck assemblies are provided with spindles that are readily couplable into the drills with which they are used. Once the assembly is separated from the drill, a technician rotates the spindle while holding the chuck housing stable in order to cause the desired locking/unlocking movement of the chuck jaws. One benefit of a removable chuck is that the technician changing cutting accessories is not subjected to the shock associated with the power locking/unlocking of the chuck. Another advantage of this arrangement is that chucks can be preloaded with cutting accessories to allow the surgeon rapidly switch the cutting accessory that is being used to perform a surgical procedure.

However, there is some difficulty associated with manual locking/unlocking currently available chucks. This difficulty is due to the fact that the drive spindle of a chuck is a relatively small and thin component, less than 0.4 inches (1.0 cm) wide and less than 2 inches (5.0 cm) long. Consequently, it is not easy for an individual to get a good grip on this component in order to turn it or hold it static in order to accomplish the desired locking of the associated jaws. This, in turn, has made it difficult for surgical personnel to provide surgeons with chuck assemblies with cutting accessories that have already been locked in place for use.

SUMMARY OF THE INVENTION

This invention is directed to a new and useful keyless chuck assembly for a rotary driven tool. The keyless chuck assembly of this invention includes a spindle lock assembly that is located between the chuck housing and the tool to which the assembly is attached. A drive shaft internal to the spindle lock assembly transfers the rotary power developed by the tool to the drive spindle. A lock prevents the drive shaft and drive spindle from rotating. By engaging the lock, it becomes a relatively simple task to manually lock a cutting accessory to the chuck. The lock is also designed to prevent its inadvertent engagement when the tool is being actuated. The spindle lock assembly of this invention is further configured to lock the drive spindle so as to prevent its rotation regardless of the angular orientation of the drive spindle to the static components of the spindle lock assembly.

BRIEF DESCRIPTION OF THE DRAWINGS

The invention is pointed out with particularity in the claims. The above and further advantages of the invention may be better understood by reference to the following detailed description, taken in conjunction with the accompanying drawings, in which:

DETAILED DESCRIPTION

Figure 1:
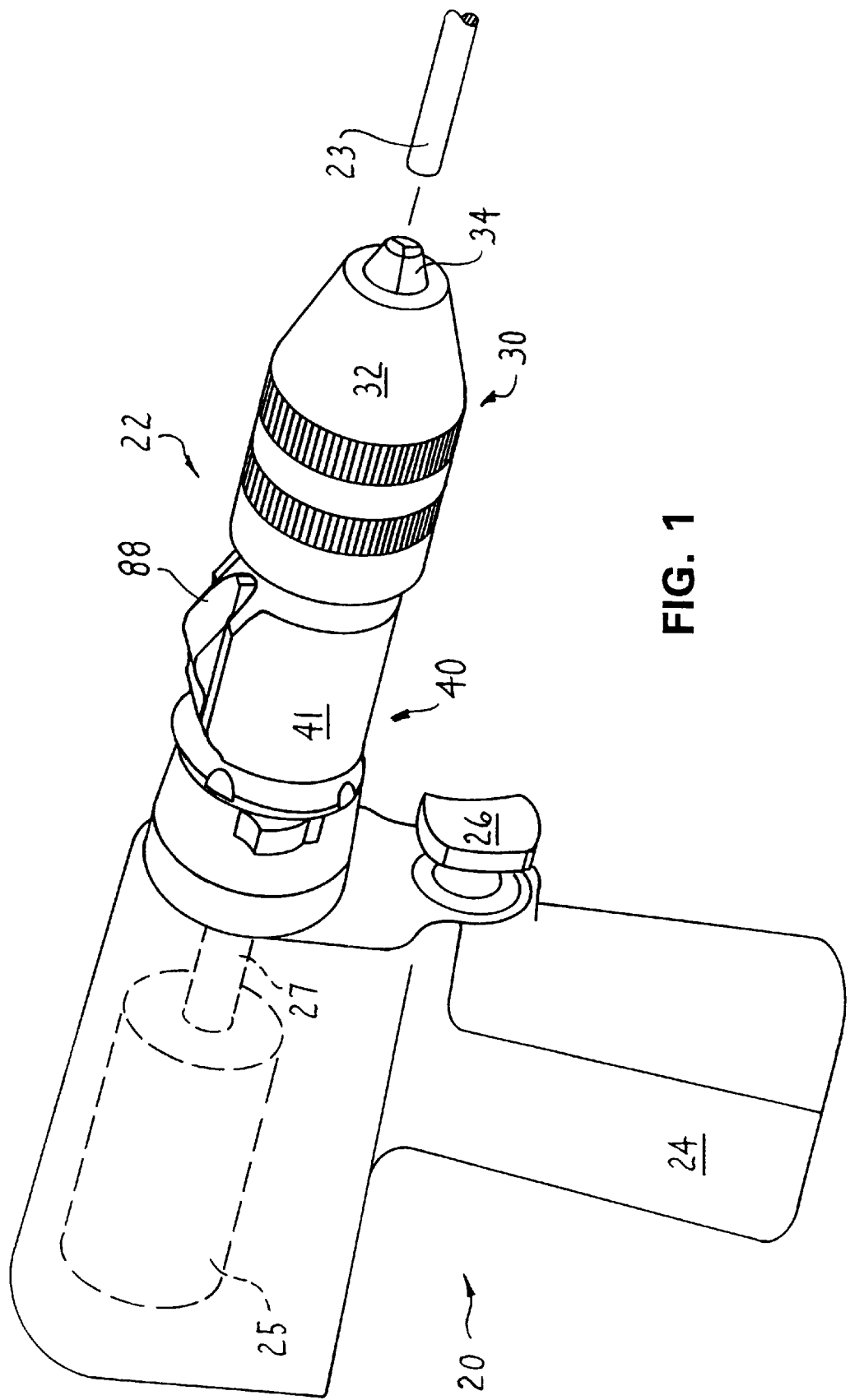
FIG. 1 is a perspective View of a tool, in particular a surgical tool, to which a keyless chuck assembly of this invention is attached.

FIG. 1 depicts a tool, in particular a surgical drill 20, to which a keyless chuck assembly 22 of this invention is attached. The drill 20 includes a housing 24, in which a motor 25 (shown in phantom) and a drive shaft 27 (shown in phantom) are. Depression of a trigger switch 26 mounted to the housing 24 results in the actuation of the motor 25 and the subsequent rotation of the drill drive shaft 27. One such version of drill 20 is the System 4 Rotary Handpiece marketed by the Stryker Corporation of Kalamazoo, Mich. as Part No. 4103.

Figure 2:
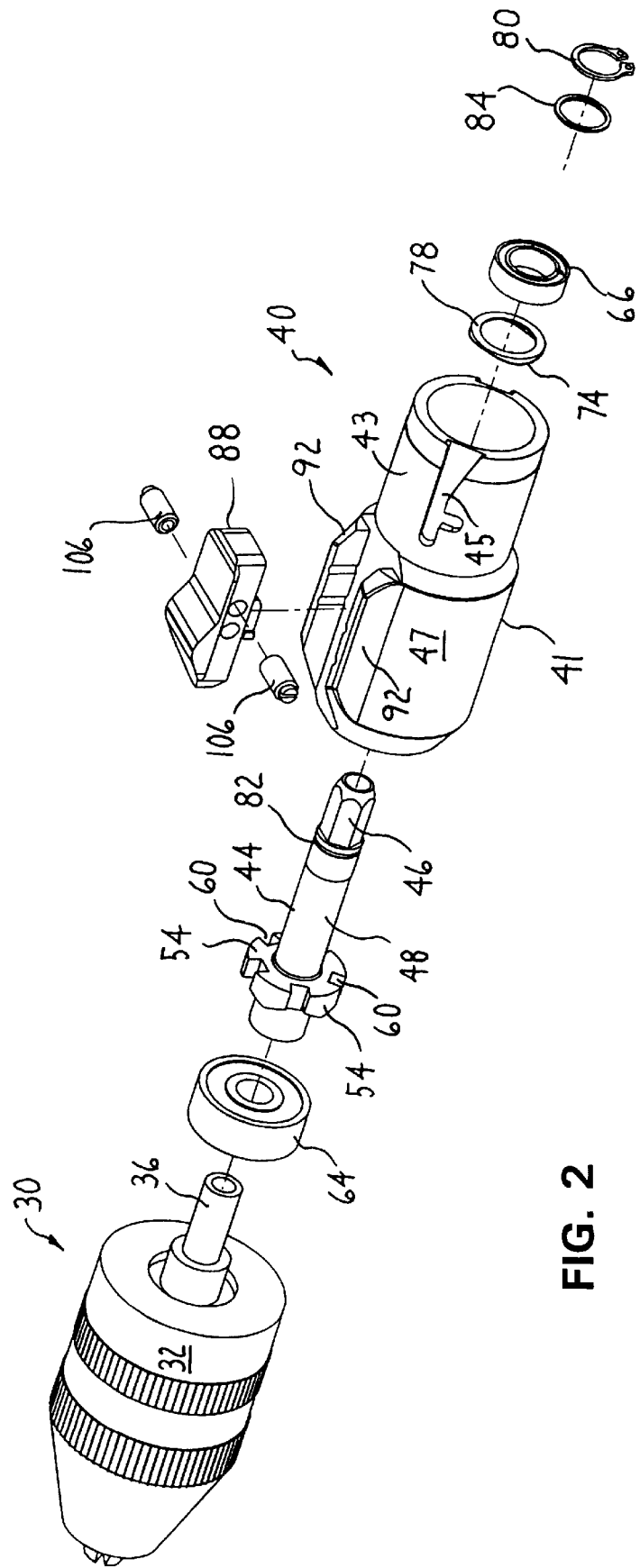
FIG. 2 is an exploded view of the keyless chuck assembly.

The keyless chuck assembly 22 is used to hold a cutting accessory 23 so that the cutting accessory 23 rotates with the actuation of the drill motor 25. The most forward subassembly of chuck assembly 22, relative to drill 20, is a chuck head 30. Chuck head 30 can be any conventional keyless chuck head. One such chuck head is available from the Snap-on Medical Products Company of Kenosha, Wis. As seen from FIGS. 1 and 2, the chuck head 30 includes a generally circular housing 32. Three jaws 34, extend from the open front end of the housing 32. The jaws 34, which are shown abutting in FIG. 1, provide the clamping force that holds the cutting accessory 23 to the chuck. A drive spindle 36 extends rearwardly from the back of the housing 32. When the jaws 34 of the chuck 30 are clamped down against the cutting accessory 23, the drive spindle 36 and housing 32 rotate together, in unison, around a common axis. This rotation causes a like rotation of the jaws 34 and the cutting accessory 23. The drive spindle 36 is further attached to the housing 32 so that the spindle and housing can rotate relative to each other around the common axis of rotation. The jaws 34 are connected to the drive spindle 36 by a linkage assembly, (not illustrated). When the housing 32 and drive spindle 36 are rotated relative to each other, the linkage assembly causes the jaws 34 either move apart, to unlock the cutting accessory, or move together, to lock a new cutting accessory in place.

Figure 3:
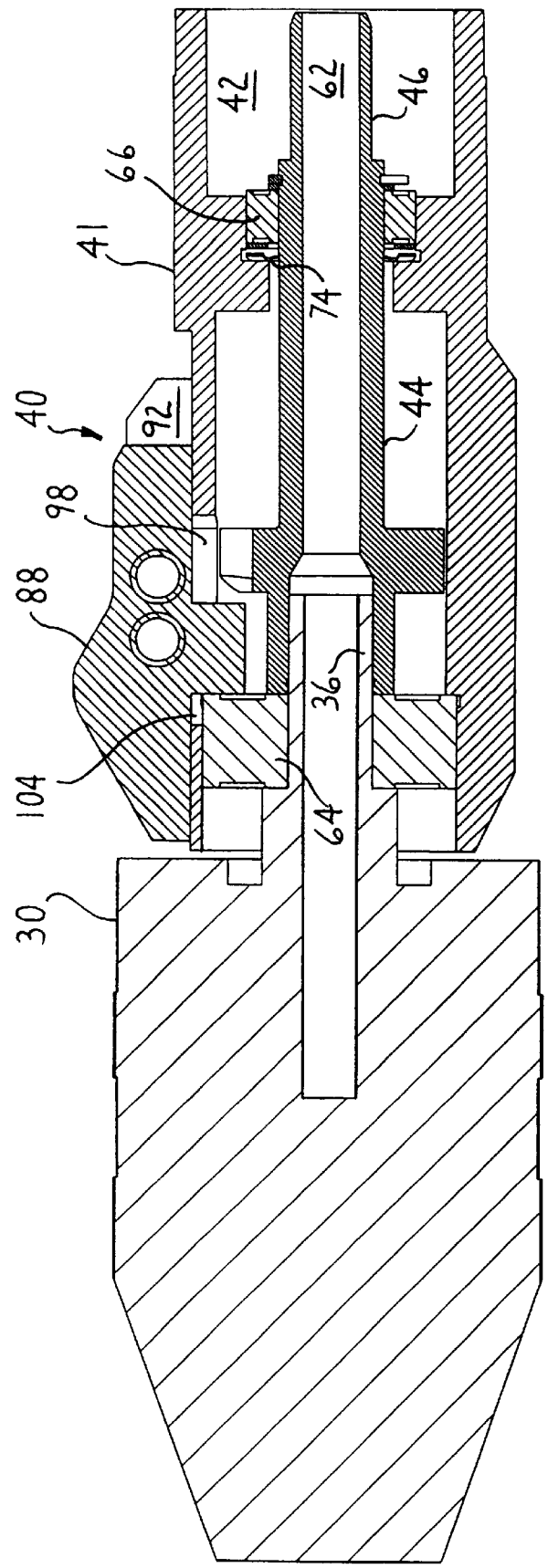
FIG. 3 is a cross sectional view of the keyless chuck assembly when the assembly is in the run state.
Figure 4:
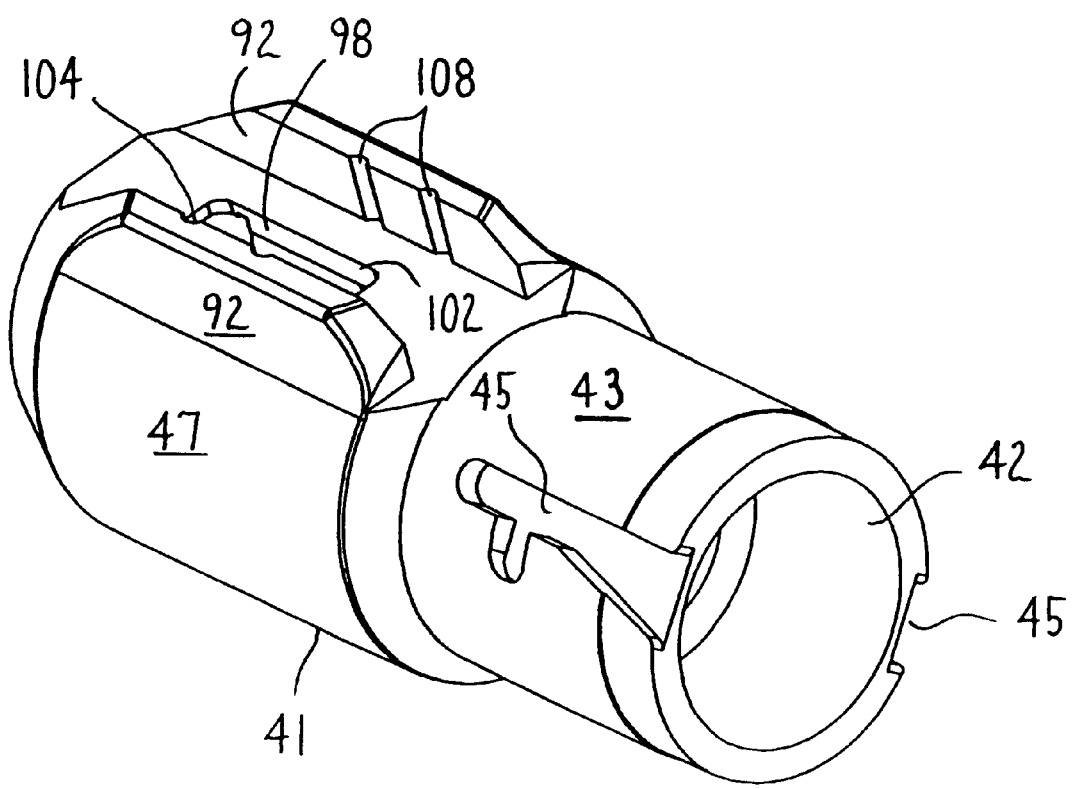
FIG. 4 is a perspective view of the housing of the spindle lock assembly.
Figure 5:
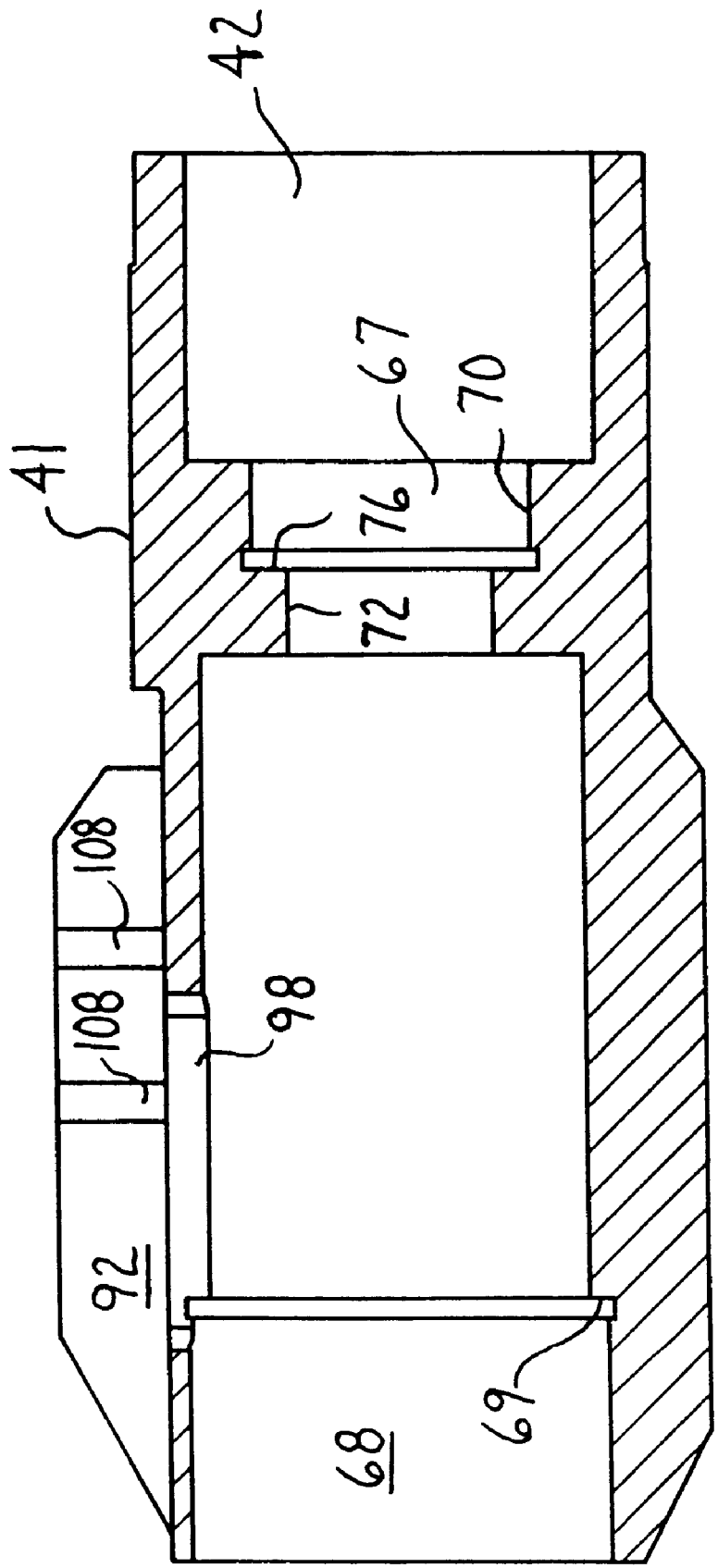
FIG. 5 is a cross sectional view of the housing of the spindle lock assembly.

The second sub-assembly of the chuck assembly 22 of this invention is the spindle lock assembly 40 which serves as the interface between the drill 20 and the chuck head 30. As illustrated in FIGS. 3, 4 and 5, spindle lock assembly 40 includes a generally tube-like housing 41 that has a multi-section bore 42 that extends axially therethrough. The housing 41 has a base section 43 that is inserted into a socket in the front face of the drill 20 with which this chuck assembly 22 is used. The base section is formed with grooves 45 in which coupling members internal to the drill 20 seat in order to hold the housing 41 to the drill and inhibit rotation of the housing. The housing 41 is further formed with a main section 47 that is located immediately forward of the base section 43. Main section 47 has an outer diameter that is slightly greater than that of the base section 43.

Figure 6:
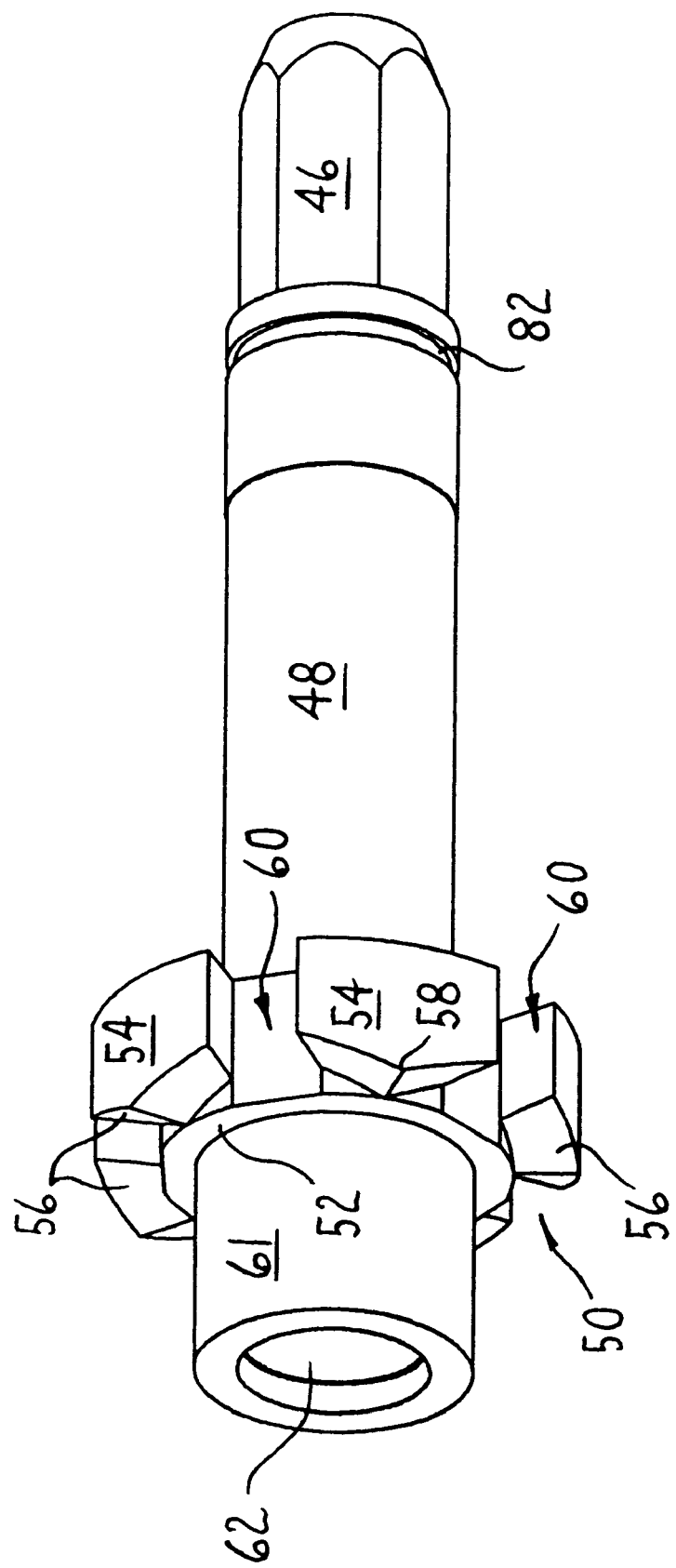
FIG. 6 is a perspective view of the drive shaft internal to the spindle lock assembly.

A drive shaft 44 is rotatably mounted in the housing 41. The drive shaft 44 transfers the rotational power of the drive shaft 27 internal to the drill 20 to the drive spindle 36 of the chuck head 30. As best seen by reference to FIGS. 3 and 6, drive shaft 44 has a butt end 46 shaped to have a polygonal cross sectional profile. This profile is adapted to facilitate the tight coupling of the drive shaft 44 into a complementary socket in the front end of the drive shaft internal to the drill 20. Extending forward from the butt end 46, (towards the cutting accessory 23,) drive shaft 44 has an elongated tube-like stem section 48.

Immediately forward of the stem section 48, drive shaft 44 is shaped to have a head section 50. The head section 50 has a reinforcing ring 52 which has an outer diameter greater than that of the stem section 48. Extending radially outwardly from reinforcing ring 52 are a plurality of spaced apart, solid tabs 54. Each tab 54 is formed to so that the forward-directed face thereof has two rearwardly directed beveled surfaces 56 that extend from a crown 58 located in the middle of the tab. Each adjacent pair of tabs 54 defines a lock slot 60 therebetween. Each beveled surface 56 leads to the side of the adjacent lock slot 60.

Extending forward from head section 50, drive shaft 44 is formed to have a cylindrical nose 61. In the depicted version of the invention, nose 61 has an outer diameter greater than that of stem section 48 and less than that of the adjacent reinforcing ring 52. The drive shaft 44 is further formed so as to have an axially extending bore 62. The drive spindle 36 of the chuck head 30 is press fit into the forward end of bore 62. Thus, the drive spindle 36 and drive shaft 44 rotate together in unison. In the depicted version of the invention, the section of the bore 62 into which the drive spindle 36 is fit, the section within nose 61, has a diameter slightly greater than that of the rest of the bore 62.

Front and rear bearing assemblies 64 and 66, respectively, rotatably hold drive spindle 36 and drive shaft 44 in housing 41. The front bearing assembly has an inner race, (not identified) that is seated over the exposed section of the drive spindle 36 seated in housing 41. Front bearing assembly 64 is seated in a large diameter front section 68 of housing bore 42. The rear face of the outer race of the front bearing assembly seats against an annular step 69 internal to the housing 41 that defines the transition between the front section 68 of bore 42 and the rest of the bore 42. The outer race of the rear bearing assembly 66 seats in a reduced diameter section 67 against the radially inwardly directed face of a first inwardly directed lip 70 internal to housing 42.

In the depicted version of the invention it will be noted from FIGS. 3 and 5 that the spindle lock assembly housing 41 is formed with a second inwardly directed lip 72 that is contiguous with and located immediately forward of the first inwardly directed lip 70. The second inwardly directed lip 72 extends further into bore 42 than the first inwardly directed lip 70. A wave spring 74 is seated against the annular step 76 that defines the transition between first and second inwardly directed lips 70 and 72, respectively. Wave spring 74 pushes rear bearing assembly 66 rearwardly. A washer 78 is located between wave spring 74 and the bearing assembly 66. A retaining ring 80 is fitted around the drive shaft 44 adjacent the rearwardly directed face of the inner race of bearing assembly 66. In the depicted version of the invention, retaining ring 80 is seated in an annular groove 82 formed in the stem section 48 of the drive shaft 44 immediately forward of the butt end 46. A washer 84 is located around the drive shaft 44 between the rear bearing assembly 66 and the retaining ring 80. The wave spring-induced rearward motion of the rear bearing assembly 66 is transferred to the drive shaft 44 through the retaining ring 80. Thus, in this version of the invention, drive shaft 44 is urged slightly rearwardly for purposes to be explained hereinafter.

Figure 7:
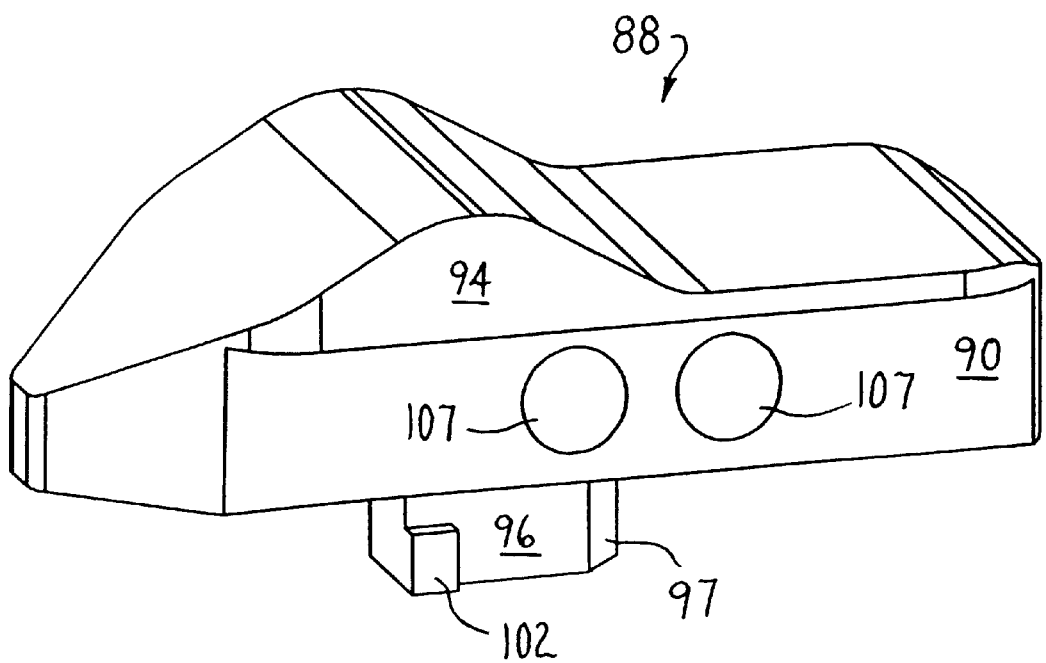
FIG. 7 is a perspective view of the switch of the spindle drive assembly.

Spindle lock assembly 40 also includes a switch 88 that is selectively positioned to inhibit movement of the drive shaft 44 and the drive spindle 36. Switch 88, now described by reference to FIGS. 2 and 7, includes a main body 90 with a generally rectangular cross sectional profile. Switch main body 90 is seated between two outwardly directed, longitudinally extending ribs 92 formed with the main section 47 of housing 41. The switch 88 also has a raised head 94 to facilitate fingertip control of the position of the switch 88.

Switch 88 has a foot 96 that extends downwardly from main body 90 into housing bore 42. The foot 96 extends through an elongated slot 98 in housing 41 located between ribs 92. The slot 98 has a greater length than foot 96 so that the switch 88 can move relative to housing 41. The foot is formed so that the rear end thereof, the end directed toward drill 20, has inwardly beveled surfaces 97, (one surface shown). The beveled surfaces 97 meet at corner located along the centerline of the foot 96.

The switch 88 is further formed so that a toe 102 extends sideways from the front end of foot 96. When the chuck assembly 22 of this invention is assembled, switch 88 is mounted to housing 41 by simultaneously inserting foot 96 through slot 98 and toe 102 in a small notch 104 integral with the front end of slot 98.

Once the chuck assembly 22 is assembled, the force imposed by wave spring 74 on the drive shaft 44 causes the front bearing assembly 64 to move under the front end of slot 98 and notch 104. This positioning of the front bearing assembly 64 effectively locks the foot 96 in bore 42 and slot 98.

The switch 88 is further provided with two ball plungers 106, one extending from each side of the main body 90. Each ball plunger 106 is seated in a separate bore 107 formed in main body 96. The ball bearings of the ball plungers 106 seat in grooves 108 formed in the side walls of ribs 92. The seating of ball bearings in grooves 108 prevents the free sliding of the switch 88.

During operation of the drill 20, the switch 88 is positioned so that foot 96 is spaced forward of tabs 54. This is the run state. Thus, when the drill 20 is actuated so as to cause the rotation of drive shaft 44 and drive spindle 36, switch 88 does not impede their rotation. The rotational power of the drive spindle 36 is directly transferred to the chuck head 30 to cause the like rotation of the cutting accessory 23.

When it is necessary to open and close the jaws 34 of the chuck head 30 to replace the cutting attachment 23 used with the drill 20, it is possible to perform the powered unlocking/locking of the chuck assembly 32 that one is able to perform with conventional chucks. Specifically, a person switching attachments 23 can hold the housing 32 of the chuck head 30 stable while simultaneously actuating the motor 25 internal to the drill 20 in order to cause the desired rotation of the drive spindle 36.

Figure 8:
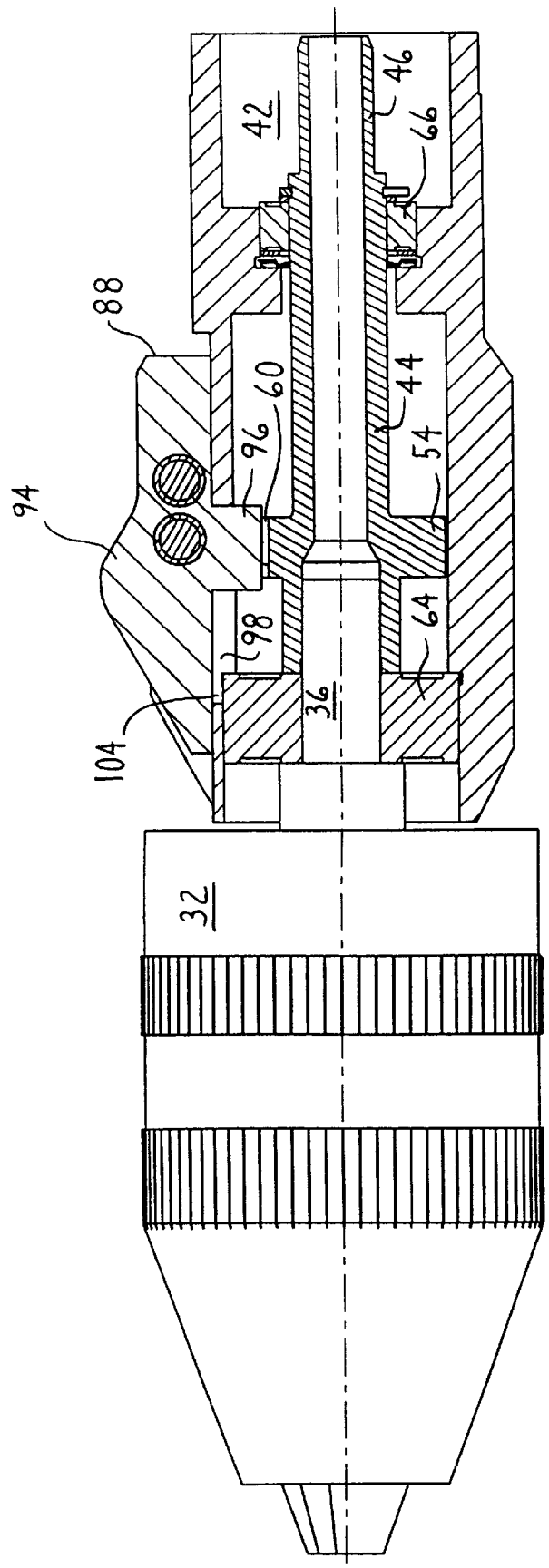
FIG. 8 is a cross sectional view of the keyless chuck assembly showing the relative position of the components when in the assembly is in the locked state.

Alternatively, the chuck assembly 20 of this invention can be unlocked/locked manually while the assembly remains coupled to the drill 20. This manual unlocking/locking occurs by first waiting for the chuck head 30 to stop rotating after the motor 25 is deactuated. Once the chuck head 30 has stopped turning, switch 88 is moved rearwardly so that foot 96 seats in one of the lock slots 60 as depicted by FIG. 8. This is the locked state. If, after the drill 20 is stopped, one of the lock slots 60 is not aligned with the path of travel of the foot 96, one of the beveled surfaces 97 of the foot will strike an adjacent one 6f the beveled surface 56 of one of the drive shaft tabs 54. Once this contact occurs, the continued manual movement of the foot 96 rearward against the tab will force the rotation of the drive shaft 44 until the foot seats in one the lock slots 60. Thus, the drive spindle 36 and drive shaft 44 do not have to be stopped in a certain select angular orientation relative to housing bore 42 in order to facilitate the prompt manual unlocking/locking of the chuck.

The seating of the switch foot 96 in a lock slot 60 blocks further rotation of the drive shaft 44. Since the chuck spindle 36 is rigidly connected to the drive shaft 44, movement of the spindle is likewise blocked. When the drill chuck assembly 22 is in this state, jaws 36 are opened and closed by the simple rotation of the chuck head housing 32. Once the new cutting accessory 23 is properly locked in place, switch 88 is moved to its forward position to allow the drill 20 to be again used in the conventional manner.

It is also relatively easy for an individual to unload and replace a cutting accessory 23 to this chuck assembly 22 when the assembly is detached from the drill 20. This is because, when the chuck assembly is so detached, the individual can use one hand to hold the spindle lock assembly housing 41 and the second hand to both center the cutting accessory and move the jaws 36 towards their closed, locked state. Then, once the cutting accessory is centered and the jaws partially locked, it is a simple two handed motion to rotate the chuck housing 32 and the spindle lock assembly housing relative to each other in order to securely lock the jaws 34 around the cutting accessory. Owing to the relatively wide diameter of the spindle lock assembly housing 41, typically between 0.75 and 1.5 inches (1.9 and 3.8 cm), and its length, between 1.5 and 3.5 inches (3.8 and 8.9 cm), it is a simple task to hold both it and the chuck housing 32 in order to be able to rotate the chuck housing relative to the drive spindle 36. The ease of performing this task makes it a relatively simple for an individual to be able to manually unlock/lock the chuck assembly 22 of this invention when the assembly is disconnected from the complementary drill 20.

There are also safety features built into the chuck assembly 22 of this invention to prevent its improper use. If a person tries to move the switch 88 from the run state to the locked state when the drill 20 is actuated, one of the beveled surfaces 97 of foot 96 will strike one of the beveled surfaces 56 of one of the rotating tabs 54. Owing to the rotational force of the rotating tab 54, the foot 96 is urged in the forward direction, away from the adjacent lock slot 60. This forward-directed displacement of the foot 96 prevents the foot from seating into a lock slot 60 while the drive shaft 44 is still rotating.

In the event someone tries to actuate the drill while the switch 88 is in the locked state, foot 96 will prevent drive shaft 44, drive spindle 36 and the drive shaft 27 integral to the drill motor 25 from rotating. This inaction will be readily apparent to the individual attempting to actuate the drill 20. This lockout of the drill drive shaft 27 which, occurs for the brief moment it takes the individual to realize the state of the chuck, does not adversely affect the subsequent operation of the drill 20 or chuck assembly 22.

It should be recognized that the foregoing description is directed to one particular embodiment of this invention and that other versions of the invention may vary from what has been described. For example, sometimes the chuck assembly 22 may be permanently mounted to the rotary driven tool with which the assembly is associated. Other means may be provided for configuring the switch so that it prevents rotation of the drive shaft. Also, in some versions of the invention, the drive spindle may extend through the spindle lock housing 41 and be the actual component that the switch selectively stops rotating. It should similarly be understood that there is no requirement that in all versions of the invention that the switch 88 be moved rearwardly in order to place the spindle lock assembly 40 in the locked state. In some versions of the invention, the lock slots in which the foot 96 integral with the switch seats may be located forward of the foot.

Moreover, it should be recognized that the components of this invention may have geometries different from what has been described. For example, the surfaces of the foot that first engage the drive lock tabs 54 may have a rounded profile as opposed to being flat. Members other than the described toe may be used to hold the foot in position. Furthermore, in some versions of the invention, the locking member may have an entirely different geometric profile than the polygonal-shaped foot. For instance, in some versions of the invention, it is contemplated that a round pin may be employed as the locking member that seats in a complementary slots in the drive shaft or drive spindle to prevent shaft/spindle rotation.

Also, it may be desirable in some versions of the invention to mount rolling balls in the base of the switch 88 that displaces the locking member. These balls provide rolling contact between the switch 88 and the underlying surface of the spindle lock housing 41. The rolling contact provided by these balls reduces the physical effort required to move switch 88 between the run and locked states.

Also, while the depicted version of the invention is shown as having six lock slots 60, other versions of the invention may have fewer or more lock slots. It may even be desirable to provide the invention with a single lock slot. In this latter version of the invention, the section of the drive shaft or drill spindle in which the lock slot is formed can be formed to have two leading surfaces, one extending from each side of the lock slot 60. As the switch locking member abuts one of these leading surfaces, this motion forces the rotation of the drive spindle 36 until the switch seats in the lock slot 60. Thus, in this version of the invention, as in the other described version of the invention the switch 88 can be actuated to prevent rotation of the drive spindle regardless of the angular orientation of the drive shaft/drive spindle in the spindle lock assembly housing 41. Therefore, it is an object of the appended claims to cover all such modifications and variations that come within the true spirit and scope of this invention.

The embodiments of the invention in which an exclusive property or privilege is claimed are defined as follows:

1. A chuck assembly for coupling an accessory to a rotary driven tool, said chuck assembly including:
   a spindle lock assembly including:
      a housing adapted to be coupled to the tool;
      a lock assembly drive shaft rotatably mounted to said spindle lock housing, said lock assembly drive shaft having a first end adapted to be coupled to a drive shaft integral with the tool and a second end distal from the first end;
      a plurality of tabs mounted to an outer surface of said spindle lock assembly drive shaft, said tabs extending circumferentially around said drive shaft and being spaced apart from each other to define a slot between each adjacent pair of tabs and each said tab shaped to have two beveled surfaces that extend rearwardly diagonally from a point forward of the slots toward the slots located on opposed of said tab; and
      a switch mounted to said housing, said switch having: a foot positioned adjacent said lock assembly drive shaft; a first position in which said foot is spaced from said tabs; and a second position in which said foot is located in one of the slots and, when said switch moves from the first position towards the second position and said foot strikes one of the beveled surfaces of one of said tabs, said drive shaft rotates to align the one slot with said foot so that said switch moves into the second position; and
   a chuck head attached to said spindle lock assembly, said chuck head having:
      a chuck housing;
      a drive spindle mounted to said chuck housing, wherein said drive spindle is connected to said spindle lock assembly drive shaft to rotate in unison with said spindle lock assembly drive shaft; and
      clamping members internal to said chuck housing for opening and closing around an accessory, wherein said chuck housing, said drive spindle and said clamping members are configured so that said drive spindle and said clamping members can rotate with said chuck head around a common axis and said drive spindle is capable of rotation relative to said chuck housing around the common axis wherein, said clamping members are connected to said drive spindle so that, if said drive spindle rotates relative to said chuck housing, said clamping members undergo an opening or closing motion.

2. The chuck assembly of claim 1, wherein:
   said foot of said switch is formed with a toe that extends laterally away from said foot, said toe being dimensioned to have a width greater than a width of the elongated slot through which said foot extends;
   said spindle lock assembly housing include a cutout formed contiguously with the slot through which said toe is inserted to mount said switch to said spindle lock assembly housing; and
   a bearing assembly is mounted in said spindle lock assembly housing to rotatably couple said spindle lock assembly drive shaft and said chuck head drive spindle to said housing, and said bearing assembly is positioned to subtend the gap through which said toe is inserted.

3. The chuck assembly of claim 1, wherein said foot of said switch has an end directed towards said tabs of said drive shaft and the end is shaped to have opposed beveled surface that extend away from a common point wherein, when the foot strikes one said tab, one of the beveled surfaces of said foot abuts one of the beveled surfaces of said tab.

4. The chuck assembly of claim 1, further including a plunger mounted to one of said switch or said spindle lock housing for engaging the other of said spindle lock housing or said switch to releasably hold said switch in the first position.

5. The chuck assembly of claim 4, wherein either said spindle lock housing or said switch is further formed so that said plunger will engage said spindle lock housing or said switch to releasably hold said switch in said first position or in said second position.

6. A rotary driven tool comprising:
   a handpiece;
   a motor internal to said handpiece, said motor having a rotating drive shaft;
   a chuck assembly mounted to said handpiece, said chuck assembly including:
      a chuck housing;
      a drive spindle that extends rearwardly from said chuck housing and that is coupled to said drive shaft to rotate in unison with said drive shaft, wherein said drive spindle is provided with a plurality of spaced apart tabs that are located circumferentially around said drive spindle, said tabs defining lock slots, each slot being located between an adjacent pair of said tabs, and each tab is formed to have two leading surfaces that extend diagonally away from the slots adjacent to said tab and the leading surfaces of said tab terminate at a common line;
      clamping members disposed in said chuck housing for opening and closing around an accessory, wherein said chuck housing, said drive spindle and said clamping members are configured to rotate in unison around a common axis and said drive spindle is capable of rotation relative to said chuck housing around the common axis wherein, said clamping members are connected to said drive spindle so that, if said drive spindle rotates relative to said chuck housing, said clamping members undergo an opening or closing motion; and a switch having a movable member that is positioned to seat in any one of the lock slots of said drive spindle for preventing rotation of said drive spindle when said drive spindle is in a plurality of rotational positions relative to said handpiece wherein, when said movable member is urged toward said tabs to be seated in one of the slots and strikes one of the leading surfaces of one said tab, subsequent movement of said movable member rotates said drive spindle to align the one slot with said movable member.

7. The rotary driven tool of claim 6, wherein said chuck assembly is removably attachable to said handpiece.

8. The rotary driven tool of claim 6, further including a spindle lock housing located between said handpiece and said chuck housing, wherein said drive spindle extends into said spindle lock housing and said switch is movably mounted to said spindle lock housing.

9. The rotary driven tool of claim 8, wherein said spindle lock housing is removably couplable to said handpiece.

10. The rotary driven tool of claim 8, wherein an intermediate drive shaft is rotatably mounted in said spindle lock housing, said intermediate drive shaft having a first end to which said motor drive shaft is attached and a second end to which said drive spindle is attached and said tabs extend from said intermediate drive shaft.

11. The rotary drive tool of claim 6, wherein said chuck assembly is configured so that, when said switch is moved towards said handpiece, said switch prevents rotation of said drive spindle.

12. The rotary driven tool of claim 6, wherein said movable member is formed with two end surfaces that are directed towards said tabs, wherein when said movable member strikes one said tabs, one of the end surfaces abuts one of the leading surfaces of said tabs and said movable member is further formed so that the end surfaces extend away from each other from a line of intersection.

13. The rotary driven tool of claim 6, wherein:

said switch is movably mounted to a housing; and a plunger is mounted to one of said switch or said spindle lock housing for engaging the other of said spindle lock housing or said switch to releasably hold said switch so that said movable member is spaced away from said drive spindle tabs.

14. A chuck assembly for removably attaching a cutting accessory to a rotary driven tool, said chuck assembly including:

a chuck housing having a front end and a rear end opposite the front end;

a drive spindle rotatably mounted to said chuck housing that extends outwardly away from the rear end of said chuck housing, said drive spindle being configured to be releasably attached to a drive shaft of the rotary driven tool, wherein said chuck housing and said drive spindle are coupled together to rotate in unison around a common axis or to rotate relative to each other around the common axis;

a clamping assembly mounted in the front end of said chuck housing for releasably holding a cutting accessory, wherein said clamping assembly is connected to said chuck housing and said drive spindle so that, when said chuck housing and said drive spindle engage in rotational motion relative to each other, said clamping assembly undergoes a locking or unlocking motion around the cutting accessory;

a spindle lock housing positioned adjacent the rear end of said chuck housing, said spindle lock housing having a bore through which said drive spindle extends and a coupling means for releasably holding said spindle lock housing to the rotary tool, wherein said drive spindle is rotatably disposed in said spindle lock housing; and a lock assembly, said lock assembly including:

a plurality of spaced apart tabs that mounted to a portion of said drive spindle located in said spindle lock housing, said tabs defining slots located between adjacent said tabs and each said tab being shaped to have two leading surfaces, each leading surface extending diagonally forward from a separate one of the slots adjacent said slot so that said leading surfaces meet forward of the slots; and a switch movably mounted to said spindle lock housing, said switch assembly having a foot located adjacent said drive spindle, said switch being selectively movable between a run position in which said foot is spaced from said tabs and a locked position in which said foot is seated in one of the slots wherein when, said switch is moved towards the locked position and said foot strikes one of the leading surfaces of one of said tabs, subsequent movement of said switch rotates said drive spindle so as to align one of the slots with said foot.

15. The chuck assembly of claim 14, wherein:

said switch foot is formed with a laterally extending toe located at one end of said foot, wherein said toe is shaped to be located entirely within the bore of said spindle lock housing;

said spindle lock housing is formed to have elongated slot through which said foot extends into the bore of said spindle lock housing, said slot having a length greater than a length of said foot less than a combined width of said foot and said toe and said spindle lock housing lock is further formed to have a cutout contiguous with the slot through which said toe of said switch is inserted into the bore of said spindle of said spindle lock housing; and a bearing assembly is mounted in the bore of said spindle lock housing for rotatably holding said drive spindle in the bore and said bearing assembly is positioned to subtend the cutout through which said toe is inserted in the bore.

16. The chuck assembly of claim 14, wherein said foot of said switch is formed with opposed end surfaces that extend away from a line of intersection, said end surface being directed to said tabs of said drive spindle so that, when said foot strikes the leading surface of one said tab one of the end surfaces abuts the leading surface of said tab.

17. The chuck assembly of claim 14, further including a plunger mounted to one of said switch or said spindle lock housing for engaging the other of said spindle lock housing or said switch to releasably hold said switch in the run position.

18. A chuck assembly for coupling an accessory to a rotary driven tool, said chuck assembly including:

a spindle lock assembly including:

a housing adapted to be coupled to the tool, said housing having an elongated slot and a cutout space formed contiguously with the slot;

a lock assembly drive shaft rotatably mounted to said spindle lock housing, said lock assembly drive shaft having a first end adapted to be coupled to a drive shaft integral with the tool and a second end distal from the first end; and a switch mounted to said housing, said switch having a foot that extends through the elongated slot in said spindle lock assembly housing and a toe that extends laterally away from said foot, said toe being dimensioned to have a width greater than the width of the elongated slot and capable to extend through the cutout space contiguous with the slot, said switch having a first position in which said foot is spaced from said spindle lock assembly drive shaft and a second position in which said foot engages said spindle lock assembly drive shaft to prevent rotation of said spindle lock assembly drive shaft; and a bearing assembly mounted in said spindle lock housing to rotatably couple said lock assembly drive shaft to said spindle lock housing housing, said bearing assembly being positioned to extend over the cutout space in said housing; and a chuck head attached to said spindle lock assembly, said chuck head having:

a chuck housing;

a drive spindle mounted to said chuck housing, wherein said drive spindle is connected to said spindle lock assembly drive shaft to rotate in unison with said spindle lock assembly drive shaft; and clamping members internal to said chuck housing for opening and closing around an accessory, wherein said chuck housing, said drive spindle and said clamping members are configured so that said drive spindle and said clamping members can rotate with said chuck head around a common axis and said drive spindle is capable of rotation relative to said chuck housing around the common axis wherein, said clamping members are connected to said drive spindle so that, if said drive spindle rotates relative to said chuck housing, said clamping members undergo an opening or closing motion.

19. A rotary driven tool comprising:

a handpiece;

a motor internal to said handpiece, said motor having a rotating drive shaft;

a chuck assembly mounted to said handpiece, said chuck assembly including:

a spindle lock housing, said spindle lock housing having an elongated slot that extends longitudinally through a portion of said housing and a cutout section that is contiguous with one section of the elongated slot;

a drive spindle that extends rearwardly from said spindle lock housing and that is coupled to said drive shaft to rotate in unison with said drive shaft, wherein said drive spindle is formed to define a plurality of spaced apart lock slots that are located circumferentially around said drive spindle;

a switch mounted to said spindle lock housing, said switch having a foot that extends through and is movable in the elongated slot of said spindle lock housing and a toe that extends laterally away from said foot, said toe having a width greater than the width of the elongated slot, said switch being movable so that said foot is selectively seatable in or spaced away from the lock slots of said drive spindle;

a bearing assembly disposed in said spindle lock housing and positioned to cover the cutout section of said spindle lock housing, said bearing assembly rotatably securing said drive spindle in said spindle lock housing;

a chuck housing located adjacent one end of said spindle lock housing; and clamping members disposed in said chuck housing for opening and closing around an accessory, wherein said chuck housing, said drive spindle and said clamping members are configured to rotate in unison around a common axis and said drive spindle is capable of rotation relative to said chuck housing around the common axis wherein, said clamping members are connected to said drive spindle so that, if said drive spindle rotates relative to said chuck housing, said clamping members undergo an opening or closing motion.

20. The tool of claim 19, wherein said chuck assembly is selectively removable from said handpiece and said drive spindle is selectively couplable to said drive shaft.

* * * * *